United States Patent [19]

Yoshii et al.

[11] 4,247,288
[45] Jan. 27, 1981

[54] METHOD AND APPARATUS FOR ROOT CANAL IRRIGATION

[75] Inventors: Eisuke Yoshii; Hiroshi Kawase, both of Tokyo, Japan

[73] Assignee: Ricoh Watch Co., Ltd., Nagoya, Japan

[21] Appl. No.: 53,250

[22] Filed: Jun. 29, 1979

Related U.S. Application Data

[63] Continuation of Ser. No. 717,484, Aug. 25, 1979, abandoned.

[30] Foreign Application Priority Data

Jun. 18, 1976 [JP] Japan .................. 51-72052

[51] Int. Cl.³ .............................................. A61C 5/02
[52] U.S. Cl. .................................... 433/224; 433/81; 128/66
[58] Field of Search .............. 433/224, 81; 128/66

[56] References Cited

U.S. PATENT DOCUMENTS

| 3,035,351 | 5/1962 | Hirsch | 433/224 |
| 3,079,690 | 3/1963 | Lodige | 433/81 |
| 3,467,083 | 9/1969 | Mattingly | 128/66 |
| 3,495,587 | 2/1970 | Freedman | 128/66 |
| 3,522,801 | 8/1970 | Robinson | 128/66 |
| 3,624,907 | 12/1971 | Brass et al. | 433/81 |
| 3,762,411 | 10/1973 | Lloyd et al. | 128/66 |
| 3,771,557 | 11/1973 | Moret et al. | 128/66 |
| 3,863,628 | 2/1975 | Vit | 128/66 |
| 3,924,335 | 12/1975 | Balamuth et al. | 128/24 A |
| 4,021,921 | 5/1977 | Detaille | 433/81 |
| 4,078,558 | 3/1978 | Woog et al. | 128/66 |
| 4,109,650 | 8/1978 | Peclard | 128/66 |

FOREIGN PATENT DOCUMENTS

| 2546687 | 4/1976 | Fed. Rep. of Germany | 433/224 |
| 1424902 | 2/1976 | United Kingdom | 433/224 |

Primary Examiner—Gene Mancene
Assistant Examiner—John J. Wilson
Attorney, Agent, or Firm—Koda and Androlia

[57] ABSTRACT

A root canal irrigation means for treating decayed teeth including a liquid vessel filled with water, antiseptic solution or some other kind of liquid, a pumping means for pumping the liquid from the liquid vessel under pressure, and a discharge needle shaped like an injection needle coupled to the outlet of the pumping means and which feeds the liquid under pressure to a dental focus when the pumping means is operated. The pumping means comprises a reciprocating pump which is coupled to the outlet of the liquid vessel.

2 Claims, 5 Drawing Figures

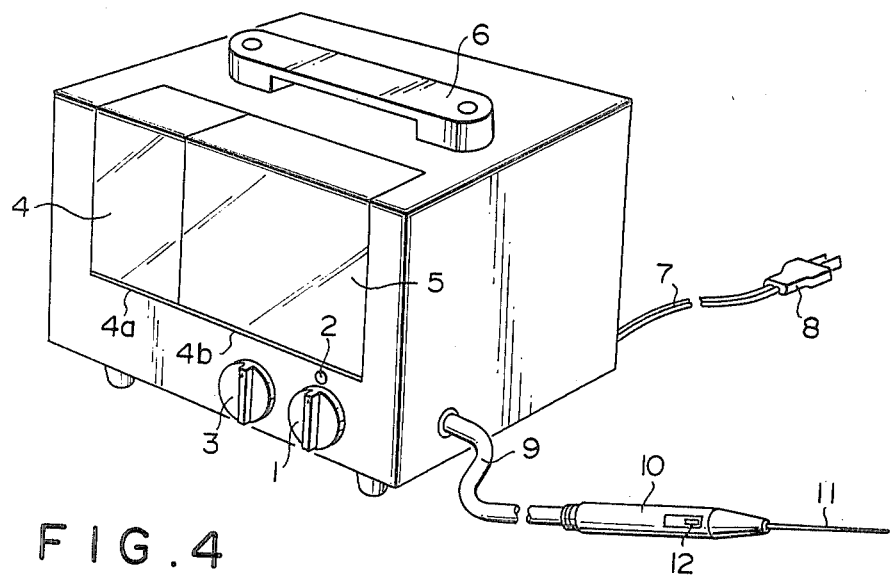
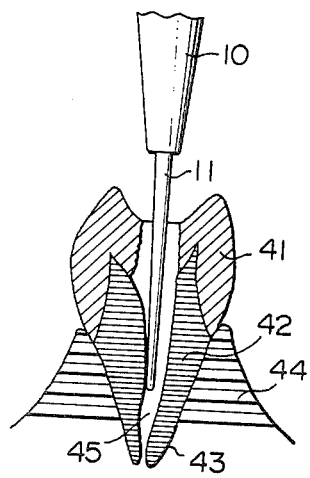
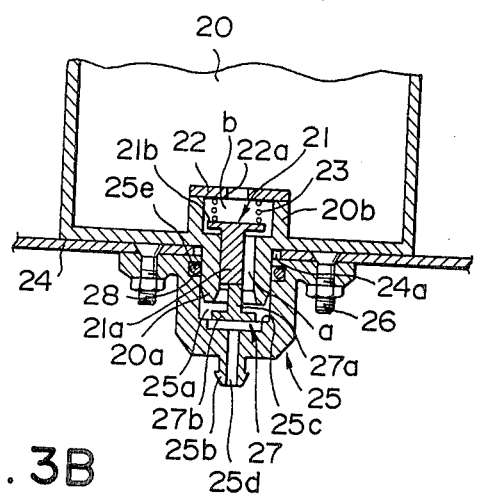
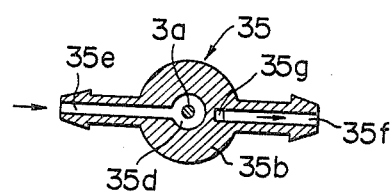

METHOD AND APPARATUS FOR ROOT CANAL IRRIGATION

This is a continuation of application Ser. No. 717,484, filed Aug. 25, 1979, and now abandoned.

BACKGROUND OF THE INVENTION

1. Field of Invention

This invention relates to a method and apparatus for root canal irrigation for treating a decayed tooth by washing the dental focus, for example, in the pulp cavity of the tooth.

2. Description of the Prior Art

Conventionally, in the treatment of a decayed tooth in the case of the extraction of the dental pulp or in the treatment of a bad tooth whose pulp is already dead and has a cavity changed into a so-called "infected root canal", the dentine thus infected in the pulp cavity must be first disinfected, and the organic materials dissolved chemically. Then, the root canal is enlarged using a reamer and a file for making removal of the infected dentine and treatment of the root canal easy. Finally, all the debris in the root canal must be washed away by means of a minyum syringe or a mechanical washer consisting of a piston and cylinder like an injection tube and a nozzle like an injection needle mounted on the tip of the piston and cylinder. By use of such means, the root canal can be washed by an experienced person. However, washing by the use of such a minyum syringe is nondiffusing in nature and therefore must be repeated again and again to produce a good washing. Accordingly, dental irrigation in this way is troublesome and not very efficient.

SUMMARY OF THE INVENTION

In view of such drawbacks, the general objects of the present invention is to provide a method and device for irrigating the root canal of a decayed tooth easily and quickly.

Another object of the present invention is to provide an improved technique for washing the root canal.

Still another object of the present invention is to provide a technique for washing the root canal which improves the effect of irrigation of the root canal.

In keeping with the principles of the present invention, the objects are accomplished by a vessel for storing water, medical fluid such as an antiseptic or some other kind of liquid, a pumping means for pumping the liquid in the vessel under pressure and a discharge needle such as an injection needle for jetting the liquid under pressure supplied by the pumping means. The root canal of the decayed tooth is irrigated with the liquid thus pumped from the discharge needle.

BRIEF DESCRIPTION OF THE DRAWINGS

The above mentioned features and objects of the present invention will become more apparent by reference to the following description taken in conjunction with the accompanying drawings, wherein like referenced numerals denote like elements, and in which:

FIG. 1 is a prospective view of a root canal irrigator in accordance with the teachings of the present invention;

FIG. 2 is a cross-sectional view of a means for coupling the vessel of FIG. 1 to a receptacle;

FIG. 3B is a cross-sectional view taken along the line B—B in FIG. 3A; and

FIG. 4 is a diagram showing how to use the root canal irrigator.

DETAILED DESCRIPTION OF THE PREFERRED EMBODIMENT

Figure 3A:
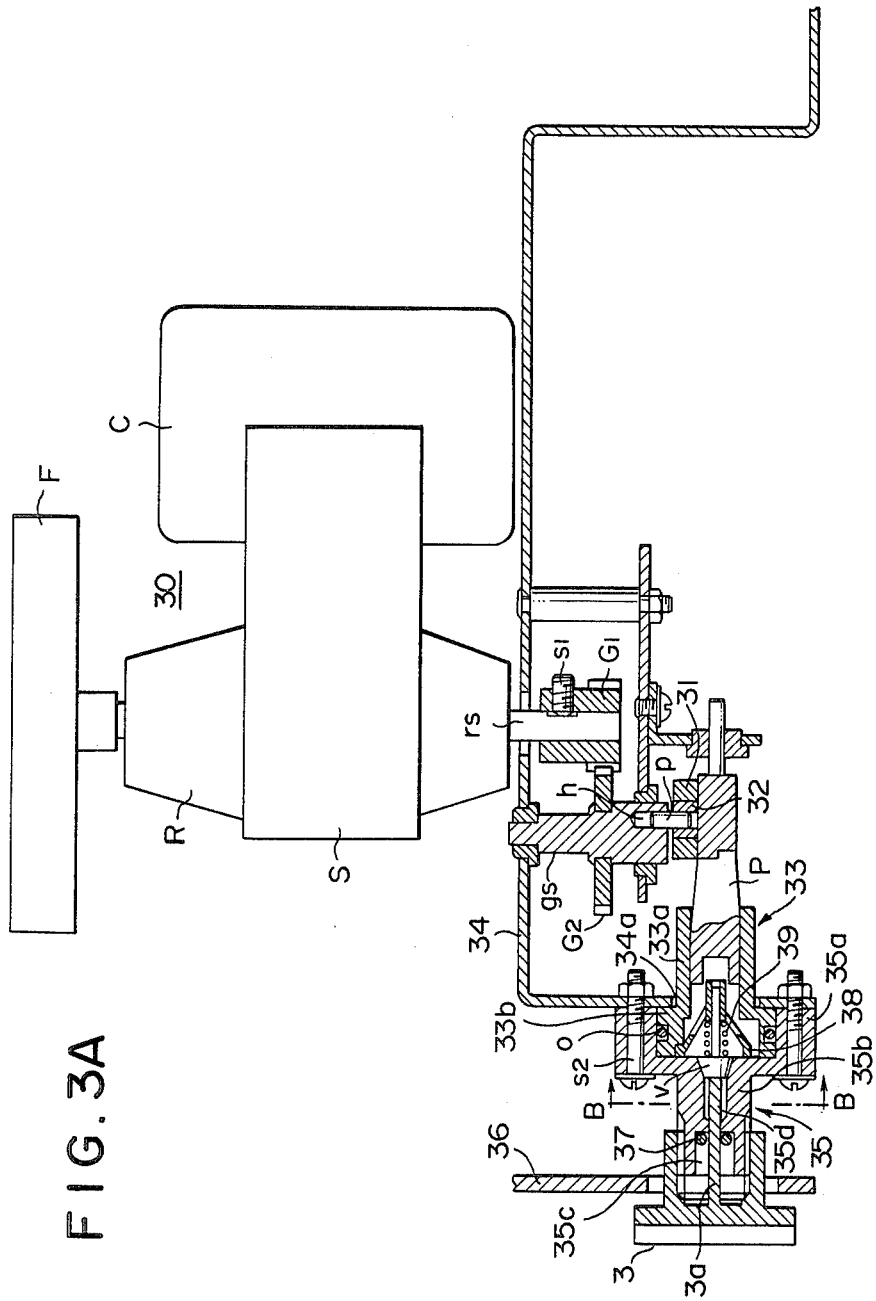
FIG. 3A is a cross-sectional view of a pumping means utilized in the embodiment of FIG. 1.

Referring more particularly to the figures, FIG. 1 is a pictorial view showing the external appearance of the root canal irrigator. Generally, the root canal irrigator of FIG. 1 houses a vessel in the left front and a pumping means coupled to the vessel for supplying liquid under pressure and a flexible tube extending from one side of the body of the irrigator and a discharge needle coupled to the end of the flexible tube. In FIG. 1, power source switch 1 turns the root canal irrigator on and off. Pilot light 2 is coupled to switch 1 and indicates the on/off condition of switch 1. Knob 3 provided in the front of the root canal irrigator is coupled to the pumping means and enables an operator to adjust the pressure of the liquid supplied to the discharge needle. Covers 4 and 5 are rotatably coupled to the front of the root canal irrigator and open outwardly along the lower side edges 4a and 4b respectively. Cover 4 is preferably made of a clear synthetic resin or the like. Inside cover 4 is formed a liquid vessel receptacle. The vessel is a cartridge type which is installed in the liquid vessel receptacle. The vessel is so constructed as to engage the liquid vessel receptacle at the bottom as shown in FIG. 2.

In FIG. 2, vessel 20 is shown partially cut away. The vessel 20 may be filled with water, a medical fluid such as an antiseptic solution or any other kind of liquid which is to be fed from the outlet port, not shown. The vessel 20 has outer and inner cylindrical protrusions 20a and 20b which extend inward and outward respectively from the bottom center of vessel 20. A cylindrical hole "a" in the outer protrusion 20a is concentric with and communicates with a cylindrical hole "b" in the inner protrusion 20b. The inner diameter of the cylindrical hole "a" is smaller than the diameter of the cylindrical hole "b". A T-shaped pin 21 is inserted into the cylindrical holes "a" and "b". The pin 21 has a cylindrical portion 21a having a diameter which is smaller than the inner diameter of cylindrical hole "a" and larger than half the diameter of cylindrical hole "a" and flange 21b shaped like a disc which has a diameter larger than the inner diameter of cylindrical hole "a" and smaller than the inner diameter of cylindrical hole "b". The axis of the cylindrical portion 21a is not aligned with the center of flange 21b. The cylindrical portion 21a and the flange 21b are held in cylindrical holes "a" and "b" respectively. Coil spring 23 is inserted between the upper face of flange 21b and the lower face of disc 22 fixed to the upper end of inner protrusion 20b. Coil spring 23 applies a resilient force to the upper side of the vessel bottom through the underside of flange 21b. Thusly, the liquid in the vessel 20 is prevented from leaking therefrom when the vessel is not set in the receptacle.

Disc 22 has a through hole 22a in the center and is fixed to the upper end of the inner protrusion 21b by an adhesive or any other suitable means. A hole 24a is made in the bottom 24 of receptacle. Bottom 24 is fixed to a dish-like coupling member 25 by screws 26 so that the hole 24a is concentric with the coupling hole 25a in coupling member 25. Coupling member 25 further has an outer protrusion 25b. Coupling hole 25a is formed concentrically with a stepped portion 25c where the diameter of the upper hole becomes larger. The outer coupling protrusion 25b has a tubular liquid feed hole 25d aligned with the coupling hole 25a. The liquid feed tube is connected to the protrusion 25b with an outwardly extending peripheral ridge.

A lid-like pin 27 is provided over the stepped portion 25c with its shaft 27a aligned with the center of the hole 24a and the coupling hole 25a. The base 27b of pin 27 is rectangularly shaped having a long side made slightly arcuate which has a diameter which allows for tight engagement with the coupling hole 25a and a short side which is smaller than the small diameter of the stepped portion 27a. The coupling hole 25a has an angular groove 25e on the upper inner surface into which an O-ring 28 is inserted.

In operation, to insert vessel 20 into the vessel receptacle, first open cover 4. When vessel 20 is inserted into the receptacle, the outer protrusion 20a of vessel 20 sets into the coupling hole 25a formed in the bottom of the receptacle. Shaft 28a of pin 27 is brought into contact with the lower end of the cylindrical portion 21a. When the outer protrusion 21a has been fully inserted into the coupling hole 25a, pin 21 is pushed upwardly against coil spring 23. As a result, liquid in the vessel 20 passes through the hollow cylindrical portions "a" and "b", coupling hole 25a and liquid feed hole 25d and flows into the liquid feed tube 25d connected detachably over the peripheral ridge 25b. The level of the liquid in the vessel 20 may be checked visually if the vessel is made of any suitable transparent material.

Referring to FIG. 1, cover 5 may be made of any synthetic resin or the like similar to cover 4. Behind cover 5 is provided a space for keeping the accessory parts for the root canal irrigator. Element 6 represents a handle coupled to the top of the irrigator. Power cord 7 with a plug 8 extends from the rear of the root canal irrigator and flexible tube 9 is detachably coupled to a holder 10 which holds various types of discharge needles which are interchangeable as necessary. Such discharge needles 11 are stored behind the cover 5 as already explained. The holder 10 is so formed as to make it easy to hold a discharge needle and irrigate a root canal. A hand switch 12 is provided on the holder 10 for greater convenience in operation.

Referring again to FIG. 1, within the root canal irrigator is provided a pumping means for pumping the liquid from the vessel 20. A typical pumping means is shown in FIG. 3A.

In FIG. 3A, the pumping means includes a motor 30 having a coil (C), a stator (S), a rotor (R) and a fan (F) for cooling the motor 30. A driving gear (G1) is fixed to the rotor shaft (rs) of the rotor (R) with a screw (S1). The driving gear (G1) engages with a follower (G2) fixed midway on the shoulder of shaft (gs) with caulking. In the enlarged portion of shaft (gs) is a hole (h) extending parallel with the axis thereof and from the lower end thereof. A pin (p) is force-fitted into all hole (h) and engages with an engaging member 31 fixed on the upper side of piston (P) through a roller 32. Thusly, rotating motions of the shaft (gs) are converted into reciprocating motions of the piston (P). Consequently, the piston (P) moves back and forth through a cylinder 33, the narrow portion 33a of which is inserted into a hole 34a made in base plate 34 and the large diameter portion 33b of the cylinder extending outwardly from the base plate 34 with a stepped portion pressed against the plate 34. On the outer surface of the large diameter portion 33b is formed a groove in which an O-ring is inserted. The large diameter portion 35a of a step cylinder member 35 is fitted onto the large diameter portion 33b, tightly covering same and is fixed to the base plate 34 with screws (S2). Knob 3, shown in FIG. 1, for adjusting the liquid pressure is mounted by screwing it onto the small diameter portion 35b of the stepped cylinder 35. Shaft 3a of knob 3 engages with the left end of a check valve (v) at the leading end thereof. Leakage between the step cylinder member 35 and the knob 3 is prevented by an O-ring 37 held between the inner surface of a hole 35c in the cylindrical member 35 and the outer surface of shaft 3a. Check valve (v) is supported by a support member 38 fixed on the cylinder 33 and is biased by a coil spring 39 against the inner surface of a truncated cone formed at the entrance of a narrow hole 35d in the cylindrical member 35. Accordingly, the pressure of the liquid in the cylinder during reciprocating motions of piston (P) can be adjusted by turning the knob 3 and moving the check valve (v) via the shaft 3a. In this manner, the pressure of the liquid supplied from the discharge needle 11 can be controlled for values between 0.2 kg/cm$^2$ and 1.2 kg/cm$^2$. Any dental focus may be irrigated to full satisfaction under the pressure of the lower value while a patient may feel rather uncomfortable when treated with liquid under the pressure of the higher value. Probably, if the higher pressure is utilized, the patient's condition may take a turn for the worse.

Utilizing the above described pump, liquid is discharged intermittently in the form of pulsating currents while the piston is reciprocating. Experiments show that such currents must be pulsated at a frequency of about 500 to 3,500 cycles per minute to make dental irrigation the most effective. Experiments further indicate that thorough washing may not be achieved at cycles higher or lower than such specific values.

Referring to FIG. 3B, shown therein is a cross-sectional view taken along a line B—B in FIG. 3A. Element 35e represents an intake port which communicates with the narrow hole 35d and to which is connected the other end of the liquid feed tube which connects to the outer ridge 25b of the coupling member 25 for supplying liquid from the vessel 20 to the cylinder. Element 35f is a drain port. Liquid under pressure resulting from the reciprocating motions of the piston (P) shown in FIG. 3A is fed to the drain port 35f through a hole 35g which communicates with the cylinder, and to the tube 9 shown in FIG. 1 and finally discharged from discharge needle 11.

With such an arrangement as described heretofore, the root canal irrigator of this invention is used as illustrated in FIG. 4, where elements 10 and 11 represent respectively the holder and the discharge needle. Element 41 represents the enamel of a tooth, 42 the dentine, 43 the cement and 44 the gingiva.

When the decay of a tooth becomes so advanced that most of the pulp is inflamed, the pulp must be removed entirely. A cavity 45 thus produced must be cleaned well and disinfected before any filler is applied to the cavity. For this purpose, discharge needle 11 is inserted into the pulp cavity 45 produced by taking out the dental pulp, and water or medicinal fluid is intermittently jetted out under the control of the power source switch 1 and the hand switch 12. The liquid thus discharged irrigates the pulp cavity 45 and washes away decayed substances. By using this irrigator it is possible for dentists to reduce the time required for washing teeth and improve the effect of dental irrigation. This treatment can be given without much dependence upon the doctor's personal skill. Furthermore, the root canal irrigator in accordance with the invention may be applied not only for irrigation but also for disinfection or other purposes by using various kinds of liquid such as water, medicinal fluids and specific solutions prepared in separate vessels.

In accordance with the invention, irrigation may be achieved thoroughly even outside the root apex as well as in the pulp cavity of a decayed tooth with a jet of pulsating liquid supplied from the discharge needle and circulated through the pulp cavity. Such irrigation can be done quite effectively even on uneven or rough surfaces or in a dental focus formed in complicated branches of the tooth.

Still furthermore, in accordance with the invention dental caries may be treated without great difficulty in a shorter time and patients will be released from frequent attendance to their dentist. Furthermore, pulpitis may be treated without personal specific skill. Also, bad teeth, which otherwise were extracted as a result of some technical difficulty in the prior art dental treatment, may be saved from extraction by using this simple method and apparatus for root canal irrigation.

In all cases, it is understood that the above described embodiment is merely illustrative of but one of the many possible specific embodiments which represent applications of the principles of the present invention. Furthermore, numerous and varied other arrangements can be readily devised in accordance with the principles of the present invention by those skilled in the art without departing from the spirit and scope of the invention.

I claim:

1. A method of irrigating a root canal of a decayed tooth for treating said decayed tooth consisting of the steps of:

washing a dental focus of said decayed tooth with a pulsating liquid selected from a group consisting of water, medical fluid, anticeptic solution and washing fluid which is contained in a detachable cartridge at a pulsating frequency and under some pressure;

maintaining said pulsating frequency in the range of 500 to 3,000 cpm; and maintaining said pressure in the range of 0.2 to 1.2 $kg/cm^2$;

whereby a washing of said root canal occurs.

2. An apparatus for irrigating the root canal of a decayed tooth consisting of:

a detachable vessel cartridge filled with a liquid selected from the group consisting of water, medical fluid, anticeptic solution and washing fluid, said vessel being removable from said apparatus for replacement with a fresh filled vessel when empty;

an outlet valve means provided in said vessel and a cooperating assembly provided in the apparatus, said valve means being actuated by said cooperating assembly when said vessel is coupled to said apparatus;

a reciprocating pumping means coupled to said outlet valve of said vessel for supplying a pulsating liquid at an outlet port of said pumping means at a pulsating frequency of between 500 and 3,500 cpm; and a discharge injection needle coupled to said outlet port of said pumping means for feeding said pulsating liquid to said to root canal of said decayed tooth at a pressure between 0.2 and 1.2 $kg/cm^2$.